United States Patent
Bellamy et al.

(10) Patent No.: US 6,607,752 B2
(45) Date of Patent: Aug. 19, 2003

(54) METHOD FOR THE ANHYDROUS LOADING OF NICOTINE ONTO ION EXCHANGE RESINS

(75) Inventors: Simon Andrew Bellamy, Redhill (GB); Lyn Hughes, Harleysville, PA (US)

(73) Assignee: Rohm and Haas Company, Philadelphia, PA (US)

(*) Notice: Subject to any disclaimer, the term of this patent is extended or adjusted under 35 U.S.C. 154(b) by 33 days.

(21) Appl. No.: 09/885,880

(22) Filed: Jun. 20, 2001

(65) Prior Publication Data

US 2002/0015687 A1 Feb. 7, 2002

Related U.S. Application Data

(60) Provisional application No. 60/221,028, filed on Jul. 27, 2000.

(51) Int. Cl.[7] .................................................. A61K 9/14

(52) U.S. Cl. ....................... 424/489; 424/484; 424/486; 424/487; 424/501; 514/772.1; 514/772.3; 514/772.6; 514/772.4; 514/772.5

(58) Field of Search ....................... 546/279.4; 424/484, 424/486, 487, 489, 501; 514/772.1, 772.3, 772.6, 772.4, 772.5

(56) References Cited

U.S. PATENT DOCUMENTS 3,901,248 A * 8/1975 Lichtneckert et al. .......... 131/2
5,968,368 A * 10/1999 Powell et al. ................ 210/656

* cited by examiner

Primary Examiner—James M. Spear
Assistant Examiner—Liliana Di Nola-Baron
(74) Attorney, Agent, or Firm—Joanne P. Will; Witold A. Ziarno

(57) ABSTRACT

An environmentally friendly method of loading nicotine onto cation exchange resins under anhydrous conditions is described. The method eliminates many of the processing problems that are associated with loading in aqueous media.

20 Claims, No Drawings

METHOD FOR THE ANHYDROUS LOADING OF NICOTINE ONTO ION EXCHANGE RESINS

CROSS REFERENCE TO RELATED PATENT APPLICATIONS

This is a non-provisional application of prior pending U.S. provisional application Ser. No. 60/221,028 filed Jul. 27, 2000.

BACKGROUND OF THE INVENTION

The present invention relates to a method for the loading of nicotine onto cation exchange resins under anhydrous conditions.

Nicotine is a naturally occurring alkaloid that is found in the tobacco plant, Nicotiana tobacum. It finds great use in the pharmaceutical and agricultural industries. In the pharmaceutical industry it is extensively used in smoking cessation formulations. In this use the nicotine can be administered in the form of lozenges, chewing gum, and inhalers.

When nicotine is formulated into chewing gum and lozenges it is first loaded onto a cation exchange resin which has the effect of controlling the release rate of the nicotine during chewing or sucking in the mouth. Such complexes of nicotine with ion exchange resins are the subject of GB1325011. In agriculture it is used as a pesticide; and it is formulated as the nicotine sulfate salt in water, at a 40% concentration.

The typical method for loading substances onto an ion exchange resin is to dissolve an acidic or basic, ionizable substance in water, and then mix it with a suitable ion exchange resin. The substance is absorbed into the resin by the mechanism of ion exchange. See U.S. Pat. No. 2,990,332. The extent of loading will depend on several factors, including the rate of diffusion, the equilibrium constant, temperature, and the presence of other ions. The water is then removed by filtration, and the polymeric complex dried by heating.

The use of non-aqueous solvents as media for ion exchange reactions is known. See, 'Ion Exchange Resins' by Robert Kunin, p. 310, published by Robert E. Krieger Publishing Co, 1990. However, reactions times are reported to be very long for non-swelling solvents, and the solvents typically used are not optimum for industrial scale because they are flammable, or toxic, or difficult to remove efficiently, or difficult to re-use, or environmentally unacceptable, or high cost.

In the currently used commercial processes to make the polymeric complex of nicotine, nicotine is loaded onto a ground, weakly acidic cationic ion exchange with a methacrylic backbone and carboxylic acid functionality. The loading is performed in a predominantly aqueous system, whereby the nicotine becomes immobilized on the resin by reaction with the carboxylic acid groups. Use of an aqueous system for the loading has the disadvantage that the resulting slurry has to be dewatered and dried. This is currently achieved in a number of different ways, e.g. dewater in a decanter, and then dry in a vacuum dryer; evaporate the water directly from the slurry in a vacuum distillation apparatus; or evaporate the water directly from the slurry using a spray dryer. There are problems associated with each of these methods. The decanter operation is made difficult because the cation exchange resin contains a significant fraction of very fine particles (<40 micron), and wet-cakes from such decanters can still contain >60% water by weight. The spray dryer and vacuum distillation operations are wasteful of energy because all the water is removed by conversion to water vapor. All of these methods can also lead to particle agglomeration. Avoidance of these problems by using typical organic solvents would be expected to lead to problems of toxicity from residual solvent, safety problems from flammability, and environmental problems from vapor emissions and waste disposal.

Applicants have surprisingly discovered how to load nicotine onto cation exchange resins in an anhydrous system, using a halogenated hydrocarbon solvent and a dry cation exchange resin. By performing the loading operation under such anhydrous conditions all the problems associated with dewatering are eliminated, and the cost of removing the residual water by drying can be replaced with the much lower cost of removing the halogenated hydrocarbon solvent. For example, one embodiment of the present invention uses 1,1,1,2-tetrafluoroethane (TFE). The boiling point of TFE is $-26°$ C. It is essentially benign in humans, such that it is approved by the FDA for use as the propellant in inhalers. It has been shown to be non-ozone depleting. It is non-flammable. Use of this particular non aqueous solvent allows very efficient recovery and re-use of the solvent under very mild conditions and eliminates problems of toxicity from residual solvent, safety problems from flammability, and environmental problems from vapor emissions and waste disposal.

The following terms have the following meanings herein:

The terms "loaded" and "loading," as used here-in, mean the preparation of a resinate. The amount of loading means the amount of active substance incorporated into the resinate.

The term "resinate," as used herein, means an active substance/ion exchange resin complex.

Further, ion exchange resins are characterized by their capacity to exchange ions. This is expressed as the "Ion Exchange Capacity." For cation exchange resins the term used is "Cation Exchange Capacity." The ion exchange capacity is measured as the number equivalents of an ion that can be exchanged and can be expressed with reference to the mass of the polymer (herein abbreviated to "Weight Capacity") or its volume (often abbreviated to "Volume Capacity"). A frequently used unit for weight capacity is "milliequivalents of exchange capacity per gram of dry polymer." This is commonly abbreviated to "meq/g."

Ion exchange resins are manufactured in different forms. These forms can include spherical and non-spherical particles with size in the range of 0.001 mm to 2 mm. The non-spherical particles are frequently manufactured by grinding of the spherical particles. Products made in this way typically have particle size in the range 0.001 mm to 0.2 mm. The spherical particles are frequently known in the art as 'Whole Bead.' The non-spherical particles are frequently known in the art as 'Powders.'

STATEMENT OF THE INVENTION

The present invention relates to a method for loading nicotine onto cation exchange resins under anhydrous conditions comprising the steps:

a. preparing a nicotine/cation exchange resin/solvent mixture by blending said nicotine and cation exchange resin and said solvent together at a pressure and temperature that maintains said solvent in the liquid state, b. maintaining said mixture, at a pressure and temperature that maintains said solvent in the liquid state, for 1 second to 48 hrs., c. evaporating said solvent from said mixture to obtain a nicotine-loaded resin.

DETAILED DESCRIPTION OF THE INVENTION

The present invention relates to a method for loading nicotine onto cation exchange resins under anhydrous conditions comprising the steps:

a. preparing a nicotine/cation exchange resin/solvent mixture by blending said nicotine and cation exchange resin and said solvent together at a pressure and temperature that maintains said solvent in the liquid state, b. maintaining said mixture, at a pressure and temperature that maintains said solvent in the liquid state, for 1 second to 48 hrs., c. evaporating said solvent from said mixture to obtain a nicotine-loaded resin.

Ion Exchange resins useful in the practice of the present invention include, but are not limited to, styrenic strongly acidic cation exchange resins with sulfonic or phosphonic acid functionalities having a weight capacity of 0.1 to 8 meq/g, and styrenic weakly acidic cation exchange resins with carboxylic or phenolic acid functionalities having a weight capacity of 0.1 to 8.5 meq/g, and acrylic or methacrylic weakly acidic cation exchange resins with a carboxylic or phenolic acid functionality having a weight capacity of 0.1 to 14 meq/g, that are suitable for human and animal ingestion.

Preferred cationic exchange resins include, but are not limited to, styrenic weakly acidic cation exchange resin with a phenolic functionality with a weight capacity of 0.1 to 8.5 meq/g, a styrenic strongly acidic cation exchange resin with a sulfonic acid functionality with weight capacity of 0.1 to 8 meq/g, or acrylic or methacrylic weakly acidic cation exchange resin with a carboxylic acid functionality with weight capacity of 0.1 to 14 meq/g.

The more preferred cationic exchange resins include, but are not limited to, acrylic or methacrylic weakly acidic cation exchange resins with a carboxylic acid functionality with weight capacity of 0.1 to 14 meq/g.

The most preferred cationic exchange resin is a methacrylic weakly acidic cation exchange resin with a carboxylic acid functionality with weight capacity of 0.1 to 12 meq/g.

Strongly acidic and weakly acidic cation exchange resins useful in this invention are in the acid form or salt form or partial salt form.

Ion exchange resins useful in this invention are in powder or whole bead form.

The preferred ion exchange resins useful in this invention are in powder form.

The ion exchange resins used in the practice of the present invention have between 0% and 20% water.

The preferred ion exchange resins used in the practice of the present invention have between 0% and 10% water.

The most preferred ion exchange resins used in the practice of the present invention have between 0% and 5% water.

Nicotine useful in the practice of the present invention includes, but is not limited to, that derived from the extraction of nicotine from the tobacco plant *Nicotiana tobacum*.

The preferred nicotine useful in the practice of the current invention is nicotine that has an assay greater than 90% by weight.

The more preferred nicotine useful in the practice of the current invention is nicotine that has an assay greater than 95% by weight.

The most preferred nicotine useful in the practice of the current invention is nicotine that meets the purity specifications prescribed in the US Pharmacopeia USP24, p1179.

Solvents useful in the practice of the present invention include, but are not limited to, halogenated hydrocarbons, ketones, alcohols, ethers, hydrocarbons, esters, nitrites and mixtures thereof.

The preferred solvents used in the present invention are fluorohydrocarbons with boiling points at atmospheric pressure between 30° C. and −100° C.

The more preferred solvents are:

trifluoromethane ($CF_3H$);

fluoromethane ($CH_3F$);

difluoromethane ($CF_2H_2$);

1,1-difluoroethane ($CF_2HCH_3$);

1,1,1-trifluoroethane ($CF_3CH_3$);

1,1,1,2-tetrafluroethane ($CF_3CFH_2$) (TFE)

pentafluoroethane ($CF_3CF_2H$);

1,1,1,2,2-pentafluorpropane ($CF_3CF_2CH_3$);

1,1,1,2,2,3-hexafluoropropane ($CF_3CF_2CFH_2$);

1,1,1,2,3,3-hexafluoropropane ($CF_3CFHCF_2H$);.

1,1,1,3,3,3-hexafluropropane ($CF_3CH_2CF_3$);

1,1,2,2,3,3-hexafluoropropane ($CF_2HCF_2CF_2H$);

1,1,1,2,2,3,3-heptafluoropropane ($CF_3CF_2CF_2$);

1,1,1,2,3,3,3-heptafluoropropane ($CF_3CFHCF_3$);

The most preferred solvent is 1,1,1,2-tetrafluoroethane (TFE)($CF_3CFH_2$).

The solvent is removed from the final mixture either by heating to the boiling point of said solvent and removing it by distillation, or by reducing the pressure, and providing a heat source to maintain the temperature of the solution between room temperature and the atmospheric pressure boiling point of said non aqueous solvent. When said solvent has a boiling point at atmospheric pressure of approximately <0° C. it is expected to be removed essentially quantitatively at atmospheric pressure and room temperature. Such solvents can be conveniently recovered and reused by using a compressor and condenser, or a condenser at less than the boiling point of said solvent.

Loading times useful in the present invention are between 1 sec and 48 hours.

The preferred loading times useful in the invention are between 10 minutes and 18 hours.

The most preferred loading times useful in the invention are between 1 hour and 8 hours.

The preferred concentration of the nicotine to solvent useful in the practice of the invention is from 0.01% to 20% by weight of nicotine.

The more preferred concentration of the nicotine to solvent useful in the practice of the invention is from 0.1% to 10% by weight of nicotine.

The most preferred concentration of the nicotine to solvent useful in the practice of the invention is from 0.1% to 2% by weight of nicotine.

Preferably, the loading of nicotine onto the resin in the present invention is 5–100% of the ion exchange capacity of the resin, more preferably it is 10–90% of the ion exchange capacity of the resin, and most preferably it is 15–80% of the ion exchange capacity of the resin.

EXAMPLE 1—NICOTINE LOADING

Construct equipment comprising a 150 ml heavy walled glass vessel, capable of operating at more than 600 kPascals (the mix vessel) connected to a second identical vessel (the loading vessel) such that liquid in the mix vessel can be transferred into the loading vessel. Include valves and fittings in suitable places to allow complete evacuation of the system, charging of solvent (TFE) to the mix vessel, and the transfering of solvent from the mix vessel to the loading vessel. Charge 0.1 g of nicotine with an assay greater than 95% to the mix vessel, and 10 g of a dried, powder form, styrenic strongly acidic cation exchange resin with a sulfonic acid functionality with weight capacity of 4.3 to 4.9 meq/g(such as Amberlite® IRP69 available from Rohm and Haas Company, Philadelphia, Pa.) to the loading vessel. Evacuate the equipment to remove the air and then charge 50 g of solvent (TFE) to the mix vessel. The pressure will rise to about 520 kPascals due to the vapor pressure of TFE. Stir the TFE and nicotine for 5 minutes to dissolve said nicotine and then transfer the solution to the loading vessel. Mix the slurry in the loading vessel for 18 hours and then reduce the pressure in the loading vessel by venting it to the atmosphere to remove the TFE. The remaining dry solid is nicotine loaded onto the cation exchange resin.

EXAMPLE 2—TFE RECOVERY

Proceed as in Example 1, except connect the loading vessel to a 50 ml stainless steel vessel (the receiver) with a valve in between such that vapor from the loading vessel can flow into the receiver. When the loading step has been completed, evacuate the receiver and insert it in a bath of dry-ice and isopropanol (temperature approximately −68° C.). Immerse the loading vessel in a bath of water at room temperature and then slowly open the valve to the second receiver. The TFE will boil and the vapor will be condensed in the second receiver. The recovered TFE can be re-used.

EXAMPLE 3—NICOTINE LOADING

Use commercial scale equipment that allows the same operations as described in Example 1, with the addition of a compressor connected to the receiver, a condenser attached to the outlet of the compressor, and a suitable pressure vessel for storage of TFE. Charge 18 kg of nicotine that meets the purity requirements of the US Pharmacopeia 24, and charge 100 kg of a methacrylic weakly acidic cation exchange resin with a carboxylic acid functionality with weight capacity of 10.1 to 11.1 meq/g (such as Amberlite® IRP64 available from Rohm and Haas Company) to the loading vessel. Evacuate the equipment to remove the air. Seal the equipment to prevent entry of air, and then charge 360 kg of TFE to the mixing vessel. Mix the nicotine and TFE for 15 minutes to dissolve the nicotine, and then transfer the solution to the loading vessel. Mix the slurry for at least 8 hours to allow the nicotine to be absorbed by the resin. Reduce the pressure in the loading vessel to 350 kPascals by operating the compressor. The TFE will distill into the compressor. Provide heat to maintain the loading vessel at 15° C. Operate the compressor to achieve >520 kPascals at the outlet, and operate the condenser to cool the compressed TFE to 15–20° C. When all the TFE has evaporated remove the resin loaded with nicotine (118 kg) from the vessel.

What is claimed is:

1. A method for loading nicotine onto cation exchange resins under anhydrous conditions comprising the steps:
   a. preparing a nicotine/cation exchange resin solvent mixture by blending said nicotine and cation exchange resin and said solvent together at a pressure and temperature that maintains said solvent in the liquid state,
   b. maintaining said mixture, at a pressure and temperature that maintains said solvent in the liquid state, for 1 second to 48 hrs.,
   c. evaporating said solvent from said mixture to obtain a nicotine-loaded resin.

2. A method according to claim 1 wherein the solvent is a fluorohydrocarbon with a boiling point at atmospheric pressure between 30° C. and −100° C.

3. A method according to claim 1 wherein the solvent is 1,1,1,2-tetrafluorethane.

4. A method according to claim 3 wherein the concentration of nicotine to solvent is 0.01% to 20% of nicotine by weight.

5. A method according to claim 4 wherein the loading of nicotine onto the cation exchange resin is 5–100% of the ion exchange capacity of the resin.

6. A method according to claim 2 wherein said cation exchange resin is a weakly acidic resin with an acrylic or methacrylic backbone and a carboxylic acid functionality.

7. A method according to claim 6 wherein said cation exchange resin is a weakly acidic resin with a methacrylic backbone and a carboxylic acid functionality.

8. A method according to claim 6 where said cation exchange resin is in whole bead form.

9. A method according to claim 6 where said cation exchange resin is in powder form.

10. A method according to claim 6 where said cation exchange resin contains between 0% and 20% water.

11. A method for preparing nicotine containing cation exchange resin comprising: loading said nicotine onto said cation exchange resin under anhydrous conditions.

12. The method of claim 11 in which said loading further comprises: preparing a nicotine/cation exchange resin solvent mixture by blending said nicotine and cation exchange resin and a solvent together; maintaining said mixture in a liquid state; and, evaporating said solvent from said mixture to obtain a nicotine-loaded resin.

13. The method of claim 12 in which said blending further comprises blending at a pressure and temperature that maintains said solvent in a liquid state.

14. The method of claim 12 in which said maintaining said mixture further comprises maintaining said mixture at a pressure and temperature that maintains said solvent in the liquid state for 1 second to 48 hrs.

15. The method according to claim 12 wherein the solvent is a fluorohydrocarbon.

16. The method according to claim 12 wherein the solvent is 1,1,1,2-tetrafluorethane.

17. The method according to claim 11 wherein the loading of nicotine onto the cation exchange resin is 5–100% of the ion exchange capacity of the resin.

18. The method according to claim 11 wherein said cation exchange resin is a weakly acidic resin with an acrylic or methacrylic backbone and a carboxylic acid functionality.

19. The method according to claim 11 wherein said cation exchange resin is a weakly acidic resin with a methacrylic backbone and a carboxylic acid functionality.

20. A method according to claim 11 where said cation exchange resin is in whole bead form.

* * * * *